(12) United States Patent
Lee

(10) Patent No.: US 6,369,394 B1
(45) Date of Patent: Apr. 9, 2002

(54) METHOD AND APPARATUS FOR IRRADIATING A BIOLOGICAL FLUID

(75) Inventor: Eric K. Lee, Acton, MA (US)

(73) Assignee: Whatman Hemasure, Inc., Newton, MA (US)

(*) Notice: Subject to any disclaimer, the term of this patent is extended or adjusted under 35 U.S.C. 154(b) by 0 days.

(21) Appl. No.: 09/261,602

(22) Filed: Feb. 26, 1999

Related U.S. Application Data
(60) Provisional application No. 60/076,019, filed on Feb. 26, 1998.

(51) Int. Cl.[7] .......................... G01N 21/00; H01J 37/20; A61L 2/00
(52) U.S. Cl. .......................... 250/455.11; 604/4; 604/6; 422/25
(58) Field of Search .............. D24/210, 158; D10/80; 250/455.11, 273, 373; 422/25; 604/4, 6; 436/905; 378/66

(56) References Cited

U.S. PATENT DOCUMENTS

| | | | |
|---|---|---|---|
| 2,445,869 A | 7/1948 | Beyer | 155/176 |
| 4,449,050 A | 5/1984 | Kamhi | 250/455.1 |
| 4,613,322 A | 9/1986 | Edelson | 604/6 |
| 4,708,715 A | 11/1987 | Troutner et al. | 604/6 |
| 4,866,282 A | 9/1989 | Miripol et al. | 250/455.1 |
| 4,952,812 A | 8/1990 | Miripol et al. | 250/455.1 |
| 4,983,411 A | 1/1991 | Tanaka et al. | 426/234 |
| 5,120,649 A | 6/1992 | Horowitz et al. | 435/173 |
| 5,133,932 A | 7/1992 | Gunn et al. | 422/24 |
| 5,247,178 A | 9/1993 | Ury et al. | 250/438 |
| 5,290,221 A | 3/1994 | Wolf, Jr. et al. | 604/4 |
| 5,330,431 A | 7/1994 | Herskowitz | 604/153 |
| 5,459,322 A | * 10/1995 | Warkentin | 250/455.11 |
| 5,527,704 A | 6/1996 | Wolf, Jr. et al. | 435/283.1 |
| 5,557,098 A | 9/1996 | D'Silva | 250/222.1 |
| 5,587,490 A | 12/1996 | Goodrich, Jr. et al. | 549/282 |
| 5,868,695 A | 2/1999 | Wolf, Jr. et al. | 604/4 |
| 5,869,701 A | 2/1999 | Park et al. | 549/283 |
| 5,951,509 A | 9/1999 | Morris | 604/4 |

FOREIGN PATENT DOCUMENTS

| | | |
|---|---|---|
| DE | 42 09 509 C1 | 6/1993 |
| JP | 405132424 A | 5/1993 |

* cited by examiner

*Primary Examiner*—Jack Berman
*Assistant Examiner*—Kalimah Fernandez
(74) *Attorney, Agent, or Firm*—Heslin Rothenberg Farley & Mesiti P.C.; Candice J. Clement, Esq.

(57) ABSTRACT

An apparatus and method for illuminating a fluid having photosensitive material therein comprising a surface and a roller separated from the surface by a space. The space is adapted to receive a flexible container therein. The flexible container on the surface contacts the roller and the surface for translation through the space. A light source is adapted to transmit light to the space to illuminate the fluid and react with the photosensitive material as the flexible container translates through the space.

34 Claims, 3 Drawing Sheets

METHOD AND APPARATUS FOR IRRADIATING A BIOLOGICAL FLUID

PRIORITY INFORMATION

This application claims the priority of U.S. Serial No. 60/076,019, filed Feb. 26, 1998, and incorporates the same fully herein by reference.

FIELD OF THE INVENTION

The present invention relates generally to a method and apparatus for luminating a fluid. Specifically, the present invention relates to an apparatus and method that improves the efficiency and uniformity of irradiating a biological fluid, such as blood, containing a photosensitive material utilized to inactivate pathogens or the like therein.

BACKGROUND OF THE INVENTION

In recent years there has been great interest in inactivating viruses such as Hepatitis B (HBV), Hepatitis C (HCV), Human T Lymphotrophic Retrovirus Type 3 (HTLV), Human Immunodeficiency Virus (HIV), and Lymphadenopathy Associated Virus (LAV) in blood and blood products. At present, methods for inactivating these viruses in blood and blood fractions include (1) treatment with a chemical disinfectant such as formaldehyde (see U.S. Pat. No. 4,833, 165); and (2) treatment with photosensitizers. For example, U.S. Pat. No. 5,232,844 describes the use of phthalocyanines; U.S. Pat. No. 5,041,078 describes the use of sapphyrins; U.S. Pat. Nos. 4,169,204, 4,294,822, 4,328,239 and 4,727,027 describe the use of various furocoumarins (psoralens) and analogs thereof; Meruelo et al. [*Proc. Nat. Acad. Sci. U.S.*, 85, 5230–5234 (1988)] have described the use of hypericin; Lambrecht et al. [*Vox Sang.* 60, 207–213 (1991)] have described the use of phenothiazine dyes (methylene blue and toluidine blue); and U.S. Pat. No. 4,915,683 describes the use of merocyanine dyes to inactivate viruses. According to these methods, an exogenous photosensitizer is added to the blood or blood fraction and the solution is irradiated with light of appropriate wavelengths to inactivate the virus.

Phenothiazine dyes are photochemicals that bind to nucleic acids. Under suitable activation conditions such as long-wavelength UV irradiation, phenothiazine dyes are believed to crosslink the DNA and RNA strands in viruses, thereby disabling uncoiling and replication. They also react with membrane structures and they induce the production of virucidal oxygen radicals from molecular oxygen. These characteristics of phenothiazine dyes form the basis of viral inactivation and certain photochemotherapies. [See PCT application WO 91/03933.]

Psoralens are in some ways similar to phenothiazines in that activation with long-wavelength UV irradiation crosslinks the DNA and RNA strands in viruses, thereby disabling uncoiling and replication. [See Anderson and Voorhees, *Ann. Rev. Pharmacol. Toxicol.* 20, 235–57 (1980) .] More recently psoralens have been applied successfully to inactivate blood-born viruses. [See Rai, S. et al., "Dramatic Improvements in Viral Inactivation with Brominuted Psoralens, Naphthalencs and Anthracenes," *Photochem. and Photobiol.* 58:59–65 (1993).] The interaction mechanism of psoralens with DNA has been extensively studied and reviewed. A preliminary intercalation complex is formed between the psoralen and two base pairs of the duplex DNA via hydrophobic interaction. Subsequent exposure to UV-A irradiation then causes photoconjugation between the furocoumarin structure of the psoralen and one or two bases of the nucleic acid (to form mono- and bi-functional adducts, respectively). Pyrimidine bases, particularly thymine, have been identified as participants in these reactions. Subsequently, the mono-functional adduct may absorb a photon and react with a second base of the complementary strand of the DNA to form a covalent crosslink. [See Anderson and Voorhees op. cit. page 240.]

As use of photosensitizers increases, results are establishing that the effectiveness of such agents is dependent upon uniform irradiation of the fluids containing the agents. However, existing prior art methods and apparatus do not employ means that take into account this consideration and other factors for irradiating the photosensitizers. The teachings of the prior art do not sufficiently control defraction of the illumination source, do not adequately control extinction that occurs when irradiating an opaque material (e.g. red blood cells) and principally teach "open" systems where the integrity of a sealed blood system is not insured. Also, various pathogen inactivation agents such as phatholocyanine dyes, methylene blue, psoralens 2 hypericin, etc. are best activated by either ultraviolet, visible and infrared wavelength light components. For example, depending on the type of blood product desired to be irradiated, variations in the quantity of illumination must be adjustable in terms of luminance output and optical path length between fluid components due to the extinction factor. More opaque red blood cells require a sufficiently narrow space between each other to allow the blood cells at the end of the light path to receive a comparable quantity of illumination to those at the beginning of the path, without over-exposure which can damage the cells. Differently, platelet concentrates and plasma can be adequately and evenly illuminated with a much longer optical path length because they are less opaque than blood cells.

The deficiencies in the prior art are largely attributable to the failure to recognize that the optical path length between fluid components nearest an illumination source and those further away is critical to properly and effectively irradiate a fluid containing photosensitizers. Additionally, conventional means in the art of irradiating a fluid product do not provide mixing during the exposure period. Thus, uneven irradiation is problematic and more likely and the tendency to over-expose simply to achieve target levels of an activation throughout the fluid product often occurs.

A need exists for controlling the effective optical path length for irradiating a fluid. A further need exists to improve the efficiency and uniformity of biological fluid exposure to illumination. A still further need exists to reduce potential side effects to blood components due to overexposure. As will be described in greater detail hereafter, the method and apparatus of the present invention meets these needs and overcome the short comings of the prior art.

SUMMARY OF THE INVENTION

The present invention includes an apparatus for illuminating a fluid having photosensitive material therein comprising a surface. A roller is separated from the surface by a space and the space is adapted to receive a flexible container. The flexible container on the surface contacts the roller and is translated through the space. A light source is adapted to transmit light to the space to illuminate the fluid and react with photosensitive material therein as the flexible container translates through the space.

Another feature of the present invention may relate to a second roller juxtaposed from the roller and separated from the surface by a second space. In this way, the flexible container on the surface contacts the second roller after passing through the space and translates through the second space for further irradiation of the fluid, permitting successive irradiation using different wavelengths, if necessary, and benefiting the photo-chemical/blood component combination of interest.

Still another feature of the present invention may concern a second roller juxtaposed from the roller and a second support roller juxtaposed from a support roller. The second roller and second support roller are separated by a second space and the flexible container contacts the second roller and second support roller after passing through the space between the roller and support roller, for further irradiation of the fluid.

The invention also provides for a method of inducing a photoreaction of a photosensitive material within a fluid in a flexible container comprising: placing the flexible container into a well-defined space between a roller and a surface; translating the container between the roller and surface by squeezing the container through the space; and illuminating the fluid within the container as the container translates and is squeezed through the space by directing light towards the space thereby inducing photoreaction of the photosensitive material in the fluid within the container.

Yet another feature of the invention may include translating the container through a second space located between a second roller juxtaposed from the roller and the surface wherein the flexible container contacts the second roller after passing through the space and translates through the second space.

In accordance with the following it may be an advantage of the present invention to provide an adjustable optical path length for illuminating a fluid, such as the biological fluid or blood, for irradiating photosensitive material therein.

A further advantage of the invention may concern multiple locations and members for translating and illuminating a fluid in a flexible container such as a blood bag and providing efficient and uniform exposure of the fluid to the illumination source.

Yet a further advantage of the invention may concern providing sufficient mixing without having to compromise a closed system, unlike external pumping circuits and special thin-channel chambers intended to be the illumination cell. Also, mixing may be enhanced by repeated forward and reverse or reciprocating translation of a fluid container such a blood bag, and in particular for irradiation of opaque fluids such as red blood cells and the like.

Still a further advantage of the invention may include utilizing conventional biological liquid or blood collection containers, systems and methods. In this way the integrity and sterility of the collected liquid is less likely to be compromised. Also, utilizing conventional means lowers the cost of practicing the invention and simplifies use of the same.

BRIEF DESCRIPTION OF THE DRAWINGS

Other features and advantages of the invention will become more readily apparent upon a reference to the following description when taken in conjunction with the accompanying drawings, which drawings illustrate several embodiments of the invention.

DETAILED DESCRIPTION OF THE PREFERRED EMBODIMENT

Figure 1:
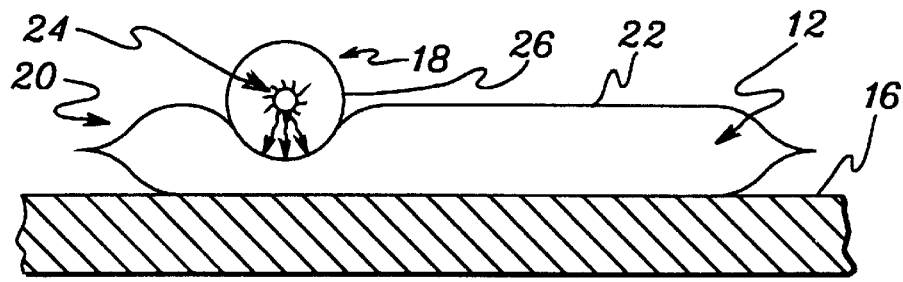
FIG. 1 is a side view of an embodiment of the apparatus in accordance with the features of the invention as a flexible container commences translation through a roller spaced from a surface.
Figure 2:
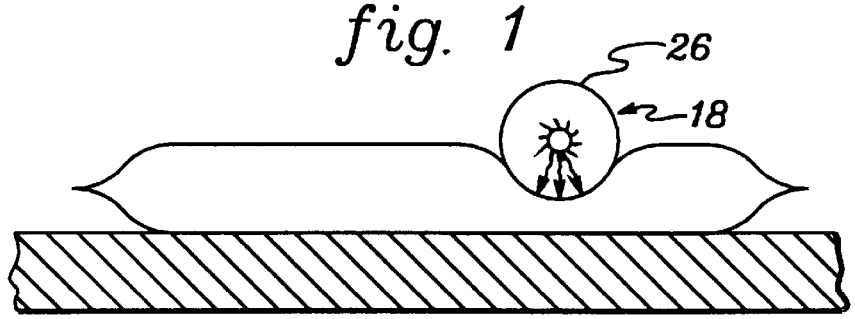
FIG. 2 is another view of the embodiment shown in FIG. 1, here with the container further translated through the space.
Figure 3:
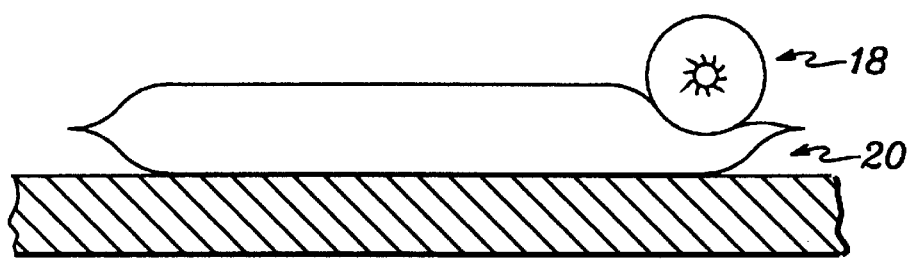
FIG. 3 is a further view of the embodiment shown in FIG. 1 with the container nearly completely translated through the space.

Referring to the drawings, the figures show the apparatus 10 for illuminating a fluid 12 having a photosensitive material typically within a fluid or biological liquid (as previously described). The apparatus comprises a surface 16 for supporting a flexible container 22. The container 22 houses the fluid 12. Excellent results are obtained when the fluid 12 comprises a biological fluid, and in particular, blood. Further, excellent results are also obtained when the flexible container 22 comprises a blood bag for holding blood therein, and in particular a standard type blood bag as known and used in the art, where blood or biological liquid is collected and stored by conventional systems and methods.

A roller 18 is separated from the surface 16 by a space 20. The roller 18 provides an illumination or light source 24 that is adapted to transmit light to the space to illuminate the fluid and react with the photosensitive material therein. The roller and the surface are orientated in relation to each other such that the flexible container can be translated through the space 20.

Figure 9:
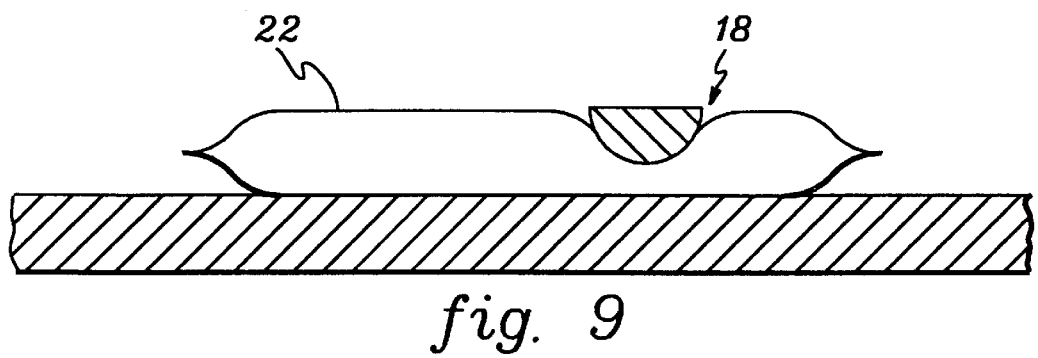
FIG. 9 is a side view of yet another embodiment of a roller, in accordance with the features of the invention.
Figure 10:
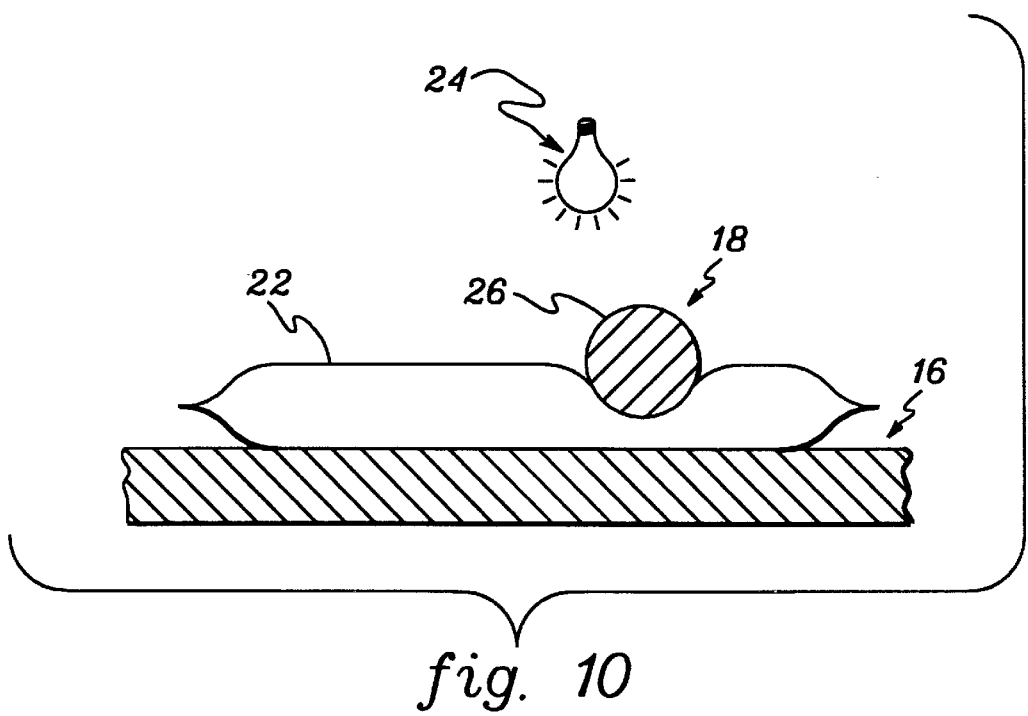
FIG. 10 is a side view of still another embodiment of a roller, in accordance with the features of the invention.

The roller could be fixed and the surface could be fixed wherein rotation of the roller translates the bag through the space. Alternatively, the roller could be fixed and the surface could be movable relative to the roller whereby the movement of the surface and/or rotational movement of the roller translates the bag through the space. Yet alternatively, the surface could be fixed and the roller rotationally, horizontally and vertically moveable relative thereto, wherein the roller travels over the container for translation of the container through the space. Also, the roller and/or surface could be reversible to translate the container manually or automatically back through the space, and repeatedly if desired. Further, another embodiment of the invention as shown in the drawings may comprise a roller shaped such that the roller is not actually round and need not necessarily rotate (for example, FIG. 9). Yet further alternatively, the light source need not be located interiorly of the roller 18 as discussed hereafter. Yet, additionally, the surface and/or the roller(s) may move in a reciprocating fashion to enhance mixing of the fluid content and/or repeat illumination passes, as desired. Yet additionally, there may be other means available for translating the bag through the space wherein such would provide substantially complete illumination exposure to the container contents and a mixing of the fluid contents as the container is translated from one end to the other through the space.

In accordance with an embodiment of the invention as generally shown in the drawings, the light source can be located interiorly of the roller. Additionally, the roller may have a light transmissive outer surface 26 wherein light can travel from the light source through the light transmissive outer surface and to the flexible container. Alternatively, in another embodiment of the invention, the light source could be located other than within the roller. Then, light would be transmitted to the fluid-filled flexible container through the roller and/or surface when the roller and/or surface has a light transmissive characteristic.

The light source 24 may transmit various wavelengths of light covering UV, visible and infrared regions, depending on the photosensitive material utilized as well as the nature of the contents desired for irradiation. Additionally, it should be understood that the apparatus could utilize other forms of irradiation, for which useful photochemical reactions may be identified. Also, this invention obtains particularly excellent results when applied for red cell pathogen inactivation based on photochemistry.

Figure 8:
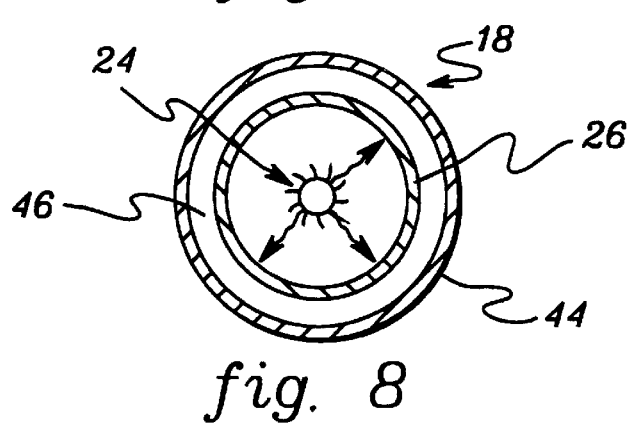
FIG. 8 is partially enlarged cut away side view taken along the line 8—8 in FIG. 7, depicting still another embodiment of a roller of the invention, here including a temperature control jacket and control medium.

Yet another feature the roller may include is temperature control means, see FIG. 8. For example, the temperature of the container 22 may be at least partially controlled by providing the roller with a temperature control jacket 44, preferably comprising a durable yet thin member that easily conducts heat, and which encloses a temperature control medium 46 such as a gas or a liquid. Together these two components act as a heat transfer medium for heating or cooling the flexible container as it translates through the space or second space, as the case may be.

Another aspect of the invention enables the space 20 to be adjusted. Excellent results are obtained when the space 20 is sized to optimize photoreactions within the flexible container in conjunction with the rate of translation of the flexible container through space 20. Together, the space and exposure time determines the overall light dose administered. As discussed previously, the desired distance between the light source and the flexible container is also dependent on other factors, for example, the photosensitive material in the fluid, the wavelength of light utilized, its intensity and the blood contents to be affected by photoreaction (platelets versus red blood cells versus plasma, etc.). Accordingly, any means known in the art could be employed to provide an adjustable space wherein the roller could be selectively positioned relative to the surface (or support roller as described herein). Preferably, photoreactions are optimized by positioning the roller to squeeze the container as it translates through the space or second space to establish the optical path length required for illumination of the fluid contents from a front side to a back of the container.

Figure 4:
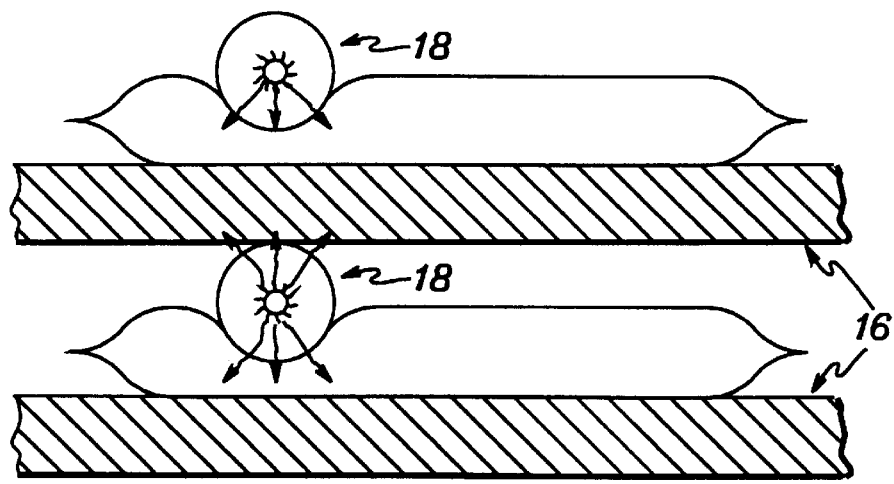
FIG. 4 is a side view of another embodiment of the invention depicting a container being translated through a space between a roller and a surface wherein the surface has a light transmissive characteristic, and where another roller and another surface are mounted below the first roller and first surface as shown.

In another embodiment of the invention the surface may have various characteristics. In particular, the surface may include a reflective characteristic wherein light passing through the flexible container and the fluid therein is reflected off of a reflective surface back into the flexible container and fluid. Alternatively, the surface 16 could include a light transmissive characteristic. For example, referring to FIG. 4, the utility of such an embodiment is shown whereby multiple containers can be translated through multiple spaces wherein the container being translated on a surface adjacent another roller obtains the advantages of illumination from both a top and a bottom side.

Figure 6:
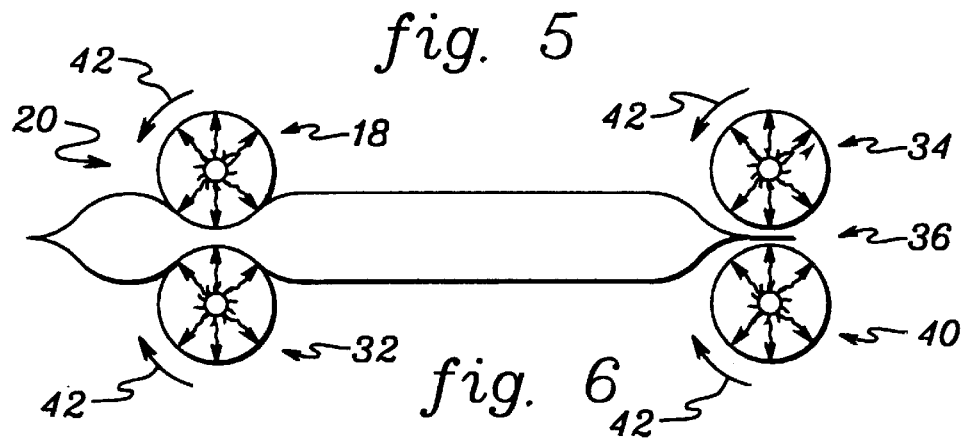
FIG. 6 is yet another embodiment in accordance with the features of the invention wherein a bag is translated through a space between a first roller and a support roller as it is translated towards a second roller juxtaposed from the first roller and which is adjacent a second support roller.
Figure 7:
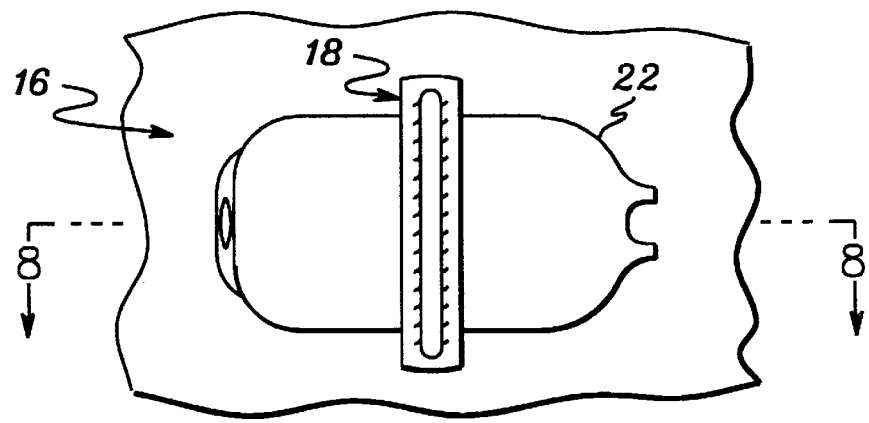
FIG. 7 is a reduced size top view of the invention shown in FIG. 2.

Yet another embodiment of the invention includes the surface 16 comprising a support roller 32. In this way, the roller 18 and/or the support roller 32 may rotate to translate the container 22 through the space 20. Alternatively, referring to FIG. 6, further excellent results are obtained with the invention when a second roller 34 is juxtaposed from the first roller adjacent a second support roller 40. The second roller 34 is spaced a second space 36 from the second support roller. This second roller and second support roller combination with the roller and support roller can provide additional illumination and translation of the container. The support roller 32, second roller 34 and second support roller 40 are typically generally constructed the same as the roller 18. The difference between these rollers is typically, substantially their location and function relative to the other components of the invention. However, if desired, differences between the rollers may exist.

Figure 5:
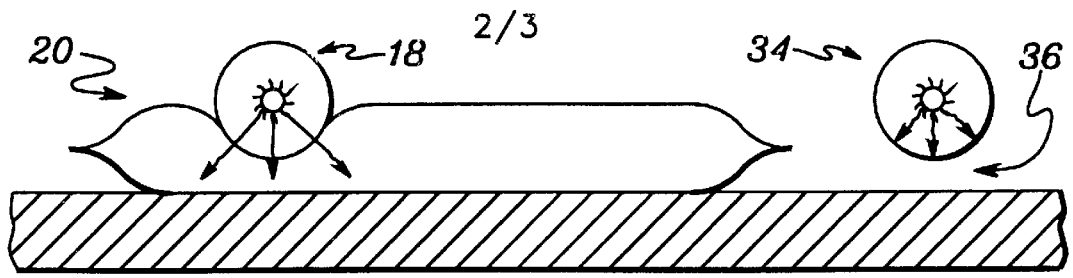
FIG. 5 is a side view of a further embodiment in accordance with the features of the invention, here depicting a bag being translated through a space between a roller and a surface as the bag translates towards a second roller juxtaposed from the first roller.

In an alternative embodiment of the invention, see FIG. 5, a second roller 34 is juxtaposed to the roller 18. The second roller is separated from the surface 16 by a second space 36. In this way, the container 22 can be translated through the space 20 and subsequently through the second space 36 for further irradiation and mixing of the contents therein.

The apparatus is used by placing the flexible container into the space 20 between the roller 18 and the surface 16. Next, the container is translated between the roller and surface through the space. Excellent results are obtained when the translation is through squeezing the container through the space 20. However, other ways to translate the container through the space could be employed and the claimed features of the invention would be utilized. A further step to this method includes illuminating the fluid within the container as the container translates through the space. In this way, the light is directed towards the space thereby inducing photoreactions of the photosensitive material within the fluid.

A further embodiment of the method of the invention (see generally FIG. 5) comprises further translating the container through the second space 36 located between the second roller 34 juxtaposed from the roller 18. The second roller is spaced from the surface 16 wherein the flexible container contacts the second roller after passing through the first space and translates through the second space. Excellent results are obtained when the second space and the first space are sized to be equivalent.

In still another embodiment of the method (see generally FIG. 6), irradiating the container 22 may be further enhanced by translating the container through the second space 36 located between the second roller 34 and the second support roller 40. Together the second roller and the second support roller are juxtaposed respectively from the roller and support roller wherein the flexible container contacts the second roller and second support roller after passing through the space between the first and second rollers. Excellent results are obtained when the translating includes reciprocating one or more of the surface and roller(s) as the container is translated through the space. This enhances mixing of the fluid and repeated irradiating, as desired.

As various possible embodiments may be made in the above invention for use of different purposes and as various changes might be made in the embodiments and methods above set forth, it is understood that all of the above matters here set forth and shown in the accompanying drawings are to be interpretative, illustrative and not in a limiting sense.

What is claimed is:

1. An apparatus for illuminating a fluid having photosensitive material therein, the apparatus comprising:
    a first surface;
    a first roller separated from the first surface by a first space, the first space being adapted to receive a flexible container containing a fluid having a photosensitive material therein, wherein the flexible container contacts the first roller and is squeezed between the first surface and the first roller as it translates through the first space; and
    a light source adapted to transmit light to the first space to illuminate the fluid and react with the photosensitive material as the flexible container translates through the first space.

2. The apparatus of claim 1, wherein the first roller rotates, wherein the flexible container is translated through the first space.

3. The apparatus of claim 1, wherein the first surface moves relative to the first roller wherein the flexible container is translated through the first space.

4. The apparatus of claim 1, wherein the first space is sized to optimize photoreactions within the flexible container.

5. The apparatus of claim 4, wherein the first space is adjustable.

6. The apparatus of claim 5, wherein the light source is disposed within the first roller and wherein the first roller comprises an effectively light transmissive material, wherein light emitted from the light source passes through the effectively light transmissive material of the first roller.

7. The apparatus of claim 6, wherein the first surface comprises an effectively light reflective material, wherein light passing through the first roller, the flexible container and the fluid therein, is reflected off the effectively light reflective material of the first surface and back into the flexible container and fluid therein.

8. The apparatus of claim 5, wherein the first surface comprises an effectively light transmissive material, wherein light emitted from the light source passes through the effectively light transmissive material of the first surface.

9. The apparatus of claim 5, wherein the first surface comprises a first support roller.

10. The apparatus of claim 9, wherein the light source is disposed within one or both of the first roller and the first support roller.

11. The apparatus of claim 1, further comprising at least a second roller separated from the first surface by a second space, wherein the flexible container contacts the second roller after translating through the first space and is squeezed between the second roller and the first surface as it translates through the second space.

12. The apparatus of claim 11, wherein the second space is equal to the first space.

13. The apparatus of claim 9, further comprising a second roller separated from a second support roller by a second space, wherein the flexible container contacts the second roller after translating through the first space and is squeezed between the second roller and the second support roller as it translates through the second space.

14. The apparatus of claim 1, wherein the fluid comprises a biological fluid.

15. The apparatus of claim 14, wherein the biological fluid comprises blood.

16. The apparatus of claim 1, wherein the flexible container comprises a blood bag.

17. The apparatus of claim 1, wherein at least the first surface is mounted to reciprocate when translating the flexible container through the first space.

18. The apparatus of claim 1, wherein at least the first roller is mounted to reciprocate when translating the flexible container through the first space.

19. The apparatus of claim 1, further comprising a temperature control means.

20. The apparatus of claim 19, wherein the temperature control means comprises a temperature control jacket surrounding the first roller and enclosing a temperature control medium.

21. A method of inducing a photoreaction of a photosensitive material in a fluid contained within a flexible container, the method comprising:
    placing a flexible container containing a fluid having a photosensitive material therein, onto a first surface and contacting the flexible container with a first roller separated from the first surface by a first space;
    squeezing the flexible container between the first roller and the first surface, wherein the container is translated through the first space; and
    providing a light source to illuminate the fluid within the flexible container as it translates through the first space, wherein the light provided induces a photoreaction of the photosensitive material in the fluid.

22. The method of claim 21, wherein one or both of the first roller and the first surface reciprocates.

23. The method of claim 21, wherein the fluid comprises a biological fluid.

24. The method of claim 23, wherein the biological fluid comprises blood.

25. The method of claim 21, further comprising the step of sizing the first space to optimize photoreactions of the photosensitive material as the flexible container translates through the first space.

26. The method of claim 25, further comprising adjusting the first space.

27. The method of claim 21, wherein the step of illuminating comprises disposing a light source within the first roller, wherein the first roller comprises an effectively light transmissive material, and wherein light emitted from the light source passes through the effectively light transmissive material of the first roller.

28. The method of claim 21, wherein the first surface comprises an effectively light reflective material.

29. The method of claim 21, wherein the first surface comprises a first support roller.

30. The method of claim 29, wherein the light source is disposed within one or both of the first roller and the first support roller.

31. The method of claim 21, further comprising squeezing the flexible container between a second roller and a second surface, wherein the second roller is separated from the second surface by a second space, wherein the flexible container contacts the second roller after translating through the first space and translates through the second space.

32. The method of claim 29, further comprising squeezing the flexible container between a second roller and a second support roller, wherein the second roller is separated from the second support roller by a second space, wherein the flexible container contacts the second roller after translating through the first space and translates through the second space.

33. The method of claim 21, further comprising the step of providing a temperature control means and controlling the temperature of the fluid within the flexible container being translated.

34. The method of claim 33, wherein the temperature control means comprises a temperature control jacket surrounding the first roller and enclosing a temperature control medium.

\* \* \* \* \*